United States Patent
Hartley et al.

(10) Patent No.: US 7,914,452 B2
(45) Date of Patent: Mar. 29, 2011

(54) METHOD AND APPARATUS FOR CONTROLLING CARDIAC THERAPY USING ULTRASOUND TRANSDUCER

(75) Inventors: Jesse W. Hartley, Lino Lakes, MN (US); Joseph M. Pastore, Woodbury, MN (US); Rodney W. Salo, Fridley, MN (US); Andrew P. Kramer, Stillwater, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 834 days.

(21) Appl. No.: 11/539,939

(22) Filed: Oct. 10, 2006

(65) Prior Publication Data

US 2008/0086036 A1    Apr. 10, 2008

(51) Int. Cl.
*A61B 8/00* (2006.01)
*A61N 1/08* (2006.01)

(52) U.S. Cl. .......................... 600/439; 600/450

(58) Field of Classification Search .................. 600/439, 600/450
See application file for complete search history.

(56) References Cited

U.S. PATENT DOCUMENTS

| | | | |
|---|---|---|---|
| 4,702,253 A | 10/1987 | Nappholz et al. | |
| 5,139,020 A | 8/1992 | Koestner et al. | |
| 5,156,154 A | 10/1992 | Valenta, Jr. et al. | |
| 5,156,157 A | 10/1992 | Valenta, Jr. et al. | |
| 5,183,040 A | 2/1993 | Nappholz et al. | |
| 5,188,106 A | 2/1993 | Nappholz et al. | |
| 5,313,949 A * | 5/1994 | Yock | 600/467 |
| 5,722,403 A * | 3/1998 | McGee et al. | 600/373 |
| 6,314,322 B1 | 11/2001 | Rosenberg | |
| 6,540,699 B1 * | 4/2003 | Smith | 600/587 |
| 6,795,732 B2 | 9/2004 | Stadler et al. | |
| 6,918,870 B1 | 7/2005 | Hunyor et al. | |
| 7,082,330 B2 | 7/2006 | Stadler et al. | |
| 7,272,435 B2 * | 9/2007 | Rowlandson | 600/513 |
| 2002/0082645 A1 * | 6/2002 | Sweeney | 607/2 |
| 2004/0162590 A1 * | 8/2004 | Whitehurst et al. | 607/17 |
| 2005/0149008 A1 | 7/2005 | Larson et al. | |
| 2005/0165298 A1 | 7/2005 | Larson et al. | |
| 2006/0122583 A1 | 6/2006 | Pesach et al. | |

OTHER PUBLICATIONS

Ellis, R. M., et al., "Left ventricular dimensions recorded by sonocardiometry", *Circ Res.*, 4(6), (Nov. 1956), pp. 684-688.

Hartley, C. J., et al., "An ultrasonic method for measuring tissue displacement: technical details and validation for measuring myocardial thickening", *IEEE Trans Biomed Eng.*, 38(8), (Aug. 1991), pp. 735-747.

Hartley, C. J., "Doppler measurement of myocardial thickening with a single epicardial transducer", *Am J Physiol.* Dec. 1983;245(6):, pp. H1066-H1072.

* cited by examiner

*Primary Examiner* — Carl H. Layno
*Assistant Examiner* — Tammie K Heller
(74) *Attorney, Agent, or Firm* — Schwegman, Lundberg & Woessner, P.A.

(57) ABSTRACT

A cardiac rhythm management (CRM) system provides for post-myocardial infarction (MI) therapy with closed-loop control using one or more ultrasound transducers sensing one or more ultrasound signals indicative of cardiac dimensions. Cardiac size parameters are produced using the one or more ultrasound signals to represent, for example, cardiac chamber diameter, cardiac chamber volume, cardiac wall thickness, infarct size, and degree of change in any of these parameters over time or between measurements. In various embodiments, such cardiac size parameters provide for titration, safety check, and acute optimization of the post-MI therapy.

32 Claims, 13 Drawing Sheets

METHOD AND APPARATUS FOR CONTROLLING CARDIAC THERAPY USING ULTRASOUND TRANSDUCER

TECHNICAL FIELD

This document relates generally to implantable medical systems and particularly to a system that controls cardiac therapy, such as pacing and neurostimulation, using ultrasonically sensed cardiac dimensions.

BACKGROUND

The heart is the center of a person's circulatory system. It includes an electromechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions result from contractions of the myocardium. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony to result in efficient pumping functions. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of myocardial tissue resulting from cardiac ischemia, a condition in which the myocardium is deprived of adequate oxygen and metabolite removal due to an interruption in blood supply caused by an occlusion of a blood vessel such as a coronary artery. The necrotic tissue, known as infracted tissue, loses the contractile properties of normal, healthy myocardial tissue. Consequently, the overall contractility of the myocardium is weakened, resulting in an impaired hemodynamic performance. Following an MI, cardiac remodeling starts with expansion of the region of infracted tissue and progresses to a chronic, global expansion in the size and change in the shape of the entire left ventricle. The consequences include a further impaired hemodynamic performance and a significantly increased risk of developing heart failure, as well as a risk of suffering recurrent MI.

For these and other reasons, there is a need to control cardiac remodeling and improve hemodynamic performance in response to MI.

SUMMARY

A cardiac rhythm management (CRM) system provides for post-MI therapy with closed-loop control using one or more ultrasound transducers sensing one or more ultrasound signals indicative of cardiac dimensions. Cardiac size parameters are produced using the one or more ultrasound signals to represent, for example, cardiac chamber diameter, cardiac chamber volume, cardiac wall thickness, infarct size, and degree of change in any of these parameters over time or between measurements. In various embodiments, such cardiac size parameters provide for titration, safety check, and acute optimization of the post-MI therapy.

In one embodiment, a system for applying electrical stimulation to a living body includes one or more implantable ultrasound transducers and an implantable medical device. The one or more implantable ultrasound transducers sense one or more ultrasound signals indicative of one or more cardiac dimensions. Each of the one or more implantable ultrasound transducers transmits a signal and receives a reflected signal associated with the transmitted signal. The implantable medical device includes a stimulation output circuit, a cardiac size analyzer, and a stimulation controller. The stimulation output circuit delivers the electrical stimulation. The cardiac size analyzer receives the one or more ultrasound signals and produces one or more cardiac size parameters using the one or more ultrasound signals. The stimulation controller includes a stimulation delivery controller and a stimulation adjuster. The stimulation delivery controller controls the delivery of the electrical stimulation using stimulation parameters. The stimulation adjuster adjusts the stimulation parameters using the one or more cardiac size parameters.

In one embodiment, an implantable lead includes a proximal end, a distal portion, and an elongate body coupled between the proximal end and the distal portion. The proximal end is configured to be coupled to an implantable medical device. The distal portion is configured to be placed in or about the heart and includes one or more ultrasound transducers. The one or more ultrasound transducers sense one or more ultrasound signals indicative of one or more cardiac dimensions. Each of the one or more ultrasound transducers transmits a signal and receives a reflected signal associated with the transmitted signal.

In one embodiment, a method for applying electrical stimulation is provided. One or more ultrasound signals indicative of one or more cardiac dimensions are sensed using one or more implantable ultrasound transducers incorporated into a distal portion of an implantable lead. One or more cardiac size parameters are produced using the one or more ultrasound signals. Delivery of the electrical stimulation is controlled using stimulation parameters. By adjusting the stimulation parameters, the effect of the electrical stimulation is maintained within a target region defined by at least one or more values of the one or more cardiac size parameters.

In another embodiment, a method for applying electrical stimulation is provided. One or more ultrasound signals indicative of one or more cardiac dimensions are sensed using one or more implantable ultrasound transducers incorporated into a distal portion of an implantable lead. One or more cardiac size parameters are produced using the one or more ultrasound signals. A specified type cardiac condition is detected using the one or more cardiac size parameters. An alert signal is produced in response to the detection of the specified type cardiac condition. In response to the alert signal, delivery of the electrical stimulation is initiated, terminated, or adjusted.

In another embodiment, a method for applying electrical stimulation is provided. The electrical stimulation is delivered. The delivery of the electrical stimulation is controlled using multiple sets of stimulation parameters, one set at a time. One or more ultrasound signals indicative of one or more cardiac dimensions are sensed while the electrical stimulation is delivered. One or more cardiac size parameters associated with the multiple sets of stimulation parameters are produced. An optimal set of stimulation parameters is selected from the multiple sets of stimulation parameters based on the one or more cardiac size parameters.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a cardiac rhythm management CRM system that delivers post-MI therapy and controls the delivery of the post-MI therapy using one or more ultrasound signals indicative of cardiac dimensions. In one embodiment, an implantable medical device delivers the post-MI therapy such as a post-MI cardiac pacing therapy or a post-MI neurostimulation therapy. One or more ultrasound transducers are each incorporated into an implantable lead coupled to the implantable medical device. By placing each of the one or more ultrasound transducers in a specified cardiac location and/or controlling its directionality, the one or more ultrasound signals provide for detection and/or estimation of cardiac size parameters. Examples of the cardiac size parameters include cardiac chamber diameter, cardiac chamber volume, cardiac wall thickness, infarct size, the change in any of these parameters over time or between measurements, and the rate of change in any of these parameters. Such cardiac size parameters are indicative of degree and progress of cardiac remodeling and/or size and expansion of infarct region. In one embodiment, the CRM system titrates the post-MI therapy by using feedback control directing the post-MI therapy towards a target defined by at least the cardiac size parameters. In another embodiment, the CRM system provides for a safety check of the post-MI therapy by preventing the post-MI therapy from unintended adverse effects indicated by the cardiac size parameters, such as increased cardiac remodeling or expanded infarct region. In another embodiment, the CRM system provides for optimization of parameters for the post-MI therapy based on a test that evaluates multiple test parameter values by their effects on the cardiac size parameters. While electrical stimulation including cardiac pacing and neurostimulation is specifically discussed as examples of the post-MI therapy, the present subject matter applies to other post-MI therapies such as drug and biologic therapies.

Figure 1:
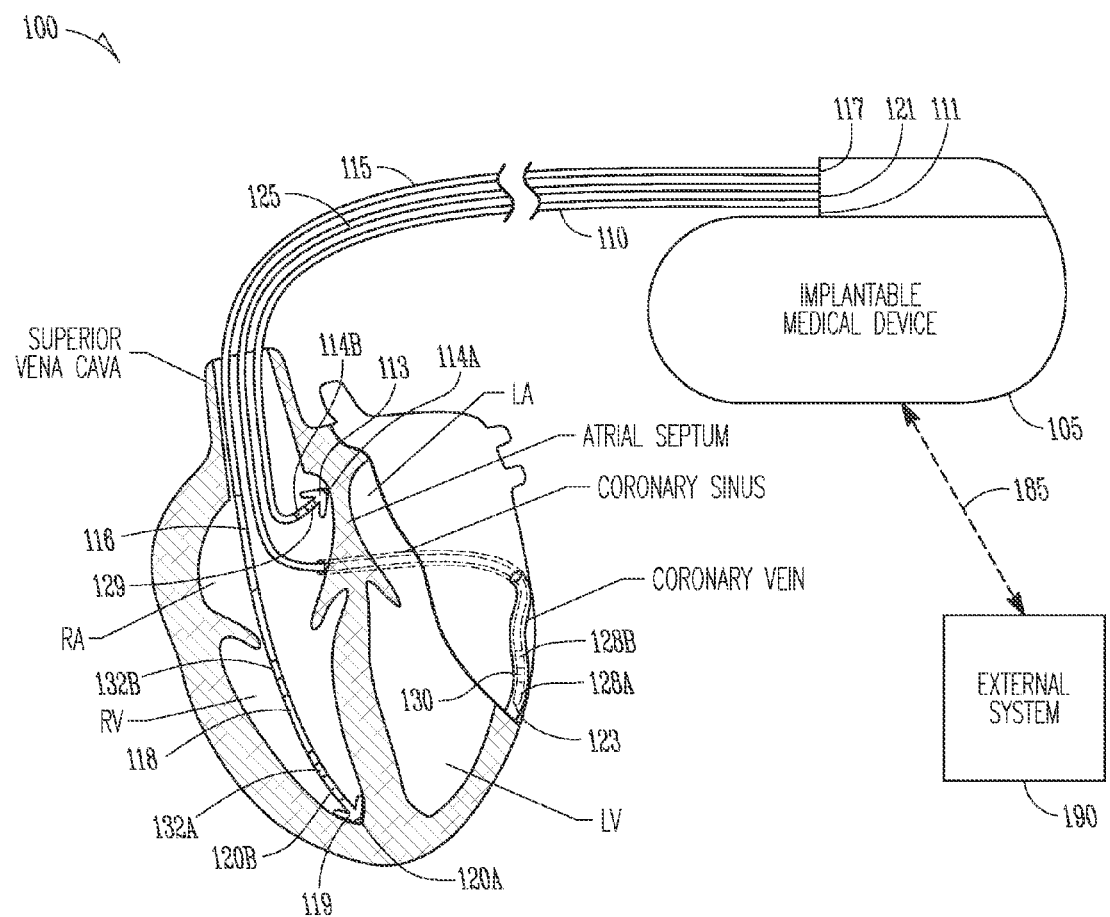
FIG. 1 is an illustration of an embodiment of a CRM system including an implantable medical device, implantable leads, and an external system and portions of an environment in which the CRM system is used.

FIG. 1 is an illustration of a CRM system 100 and portions of an environment in which system 100 operates. CRM system 100 includes an implantable medical device 105 that is electrically coupled to a heart through implantable leads 110, 115, and 125. An external system 190 communicates with implantable medical device 105 via a telemetry link 185.

Implantable medical device 105 includes a hermetically sealed can housing an electronic circuit that senses physiological signals and delivers therapeutic electrical stimulation. The hermetically sealed can also functions as an electrode for sensing and/or stimulation delivery purposes. In the illustrated embodiment, implantable medical device 105 includes a cardiac pacemaker and a cardioverter/defibrillator. In other embodiments, implantable medical device 105 includes one or more of monitoring and/or therapeutic devices such as a pacemaker, a cardioverter/defibrillator, a neurostimulator, a drug delivery device, and a biological therapy device.

Lead 110 is a right atrial (RA) pacing lead that includes an elongate lead body having a proximal end 111 and a distal end 113. Proximal end 111 is coupled to a connector for connecting to implantable medical device 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coupled to implantable medical device 105 through a conductor extending within the lead body. RA tip electrode 114A, RA ring electrode 114B, and/or the can of implantable medical device 105 allow for sensing an RA electrogram indicative of RA depolarizations and delivering RA pacing pulses. Ultrasound transducer 129 is incorporated into the distal portion of lead 110, which is the portion to be placed substantially in the RA and includes distal end 113. In one embodiment, distal end 113 is fixed onto the atrial septum.

Lead 115 is a right ventricular (RV) pacing-defibrillation lead that includes an elongate lead body having a proximal end 117 and a distal end 119. Proximal end 117 is coupled to a connector for connecting to implantable medical device 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava. Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to implantable medical device 105 through a conductor extending within the lead body. Proximal defibrillation electrode 116, distal defibrillation electrode 118, and/or the can of implantable medical device 105 allow for delivery of cardioversion/defibrillation pulses to the heart. RV tip electrode 120A, RV ring electrode 120B, and/or the can of implantable medical device 105 allow for sensing an RV electrogram indicative of RV depolarizations and delivering RV pacing pulses. Ultrasound transducers 132A-B are incorporated into the distal portion of lead 115, which is the portion to be placed substantially in the RV and includes distal end 119.

Lead 125 is a left ventricular (LV) coronary pacing lead that includes an elongate lead body having a proximal end 121 and a distal end 123. Proximal end 121 is coupled to a connector for connecting to implantable medical device 105. Distal end 123 is configured for placement in the coronary vein. Lead 125 includes an LV tip electrode 128A and an LV ring electrode 128B. The distal portion of lead 125 is configured for placement in the coronary sinus and coronary vein such that LV electrodes 128A-B are placed in the coronary vein. LV electrodes 128A and 128B are incorporated into the lead body at distal end 123 and each electrically coupled to implantable medical device 105 through a conductor extending within the lead body. LV tip electrode 128A, LV ring electrode 128B, and/or the can of implantable medical device 105 allow for sensing an LV electrogram indicative of LV depolarizations and delivering LV pacing pulses. Ultrasound transducers 130 are incorporated into the distal portion of lead 125, which is the portion to be placed substantially in the coronary vein and includes distal end 123.

In various embodiments, ultrasound transducers 130 and 132A-B each transmit an ultrasound signal and receive the ultrasound signal reflected from a boundary surface in the heart, such as the epicardial or endocardial surface of each ventricular wall. Ultrasound transducers 130 and 132A-B are each capable of sensing an ultrasound signal indicative of one or more ventricular dimensions each being a distance between two boundary surfaces in the heart. In various embodiments, such ventricular dimensions provide for measurement or estimation of cardiac chamber diameters, cardiac chamber volumes, cardiac wall thicknesses, and infarction sizes.

External system 190 allows for programming of implantable medical device 105 and receives signals acquired by implantable medical device 105. In one embodiment, telemetry link 185 is an inductive telemetry link. In an alternative embodiment, telemetry link 185 is a far-field radio-frequency telemetry link. Telemetry link 185 provides for data transmission from implantable medical device 105 to external system 190. This may include, for example, transmitting real-time physiological data acquired by implantable medical device 105, extracting physiological data acquired by and stored in implantable medical device 105, extracting therapy history data stored in implantable medical device 105, and extracting data indicating an operational status of implantable medical device 105 (e.g., battery status and lead impedance). Telemetry link 185 also provides for data transmission from external system 190 to implantable medical device 105. This may include, for example, programming implantable medical device 105 to acquire physiological data, programming implantable medical device 105 to perform at least one self-diagnostic test (such as for a device operational status), programming implantable medical device 105 to run a signal analysis algorithm (such as an algorithm implementing the tachyarrhythmia detection method discussed in this document), and programming implantable medical device 105 to deliver pacing and/or cardioversion/defibrillation therapies.

Figure 2:
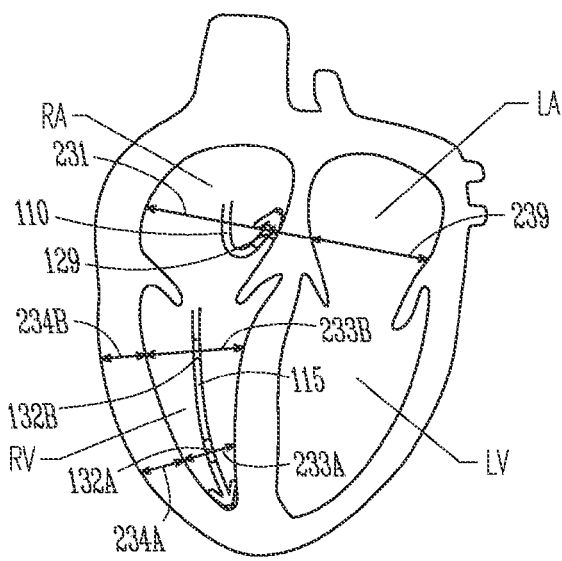
FIG. 2 is an illustration of an embodiment of portions of implantable leads for detecting cardiac dimensions using ultrasound.

FIG. 2 is an illustration of an embodiment of the distal portion of lead 110 and the distal portion of lead 115. While ultrasound transducer 129 is shown for illustrative purposes, in various embodiments, lead 110 includes any number of ultrasound transducers for placement in the RA. Ultrasound transducer 129 allows for detection of RA diameter 231 and LA diameter 239. In one embodiment, ultrasound transducer 129 is a rotating ultrasound transducer allowing for detection of atrial diameters each at various directions on a plane (i.e., single-plane atrial diameters). In one embodiment, LA dimension is used to indicate ventricular functions and/or remodeling in patients with diastolic or systolic heart failure.

While ultrasound transducers 132A-B are shown for illustrative purposes, in various embodiments, lead 115 includes any number of ultrasound transducers for placement in the RV. In one embodiment, ultrasound transducers 132A-B are each a rotating ultrasound transducer allowing for detection of ventricular diameter (233A/B) at various directions on a plane (i.e., single-plane ventricular diameters). The use of a plurality of ultrasound transducers such as 132A-B allows for estimation of the RV volume using the single-plane ventricular diameters detected at a plurality of planes each associated with one of the ultrasound transducers. Ultrasound transducers 132A-B each also allow detection of ventricular wall thickness (234A/B) at various directions on a plane. In one embodiment, use of a plurality of ultrasound transducers such as 132A-B allows for estimation of the size of an infarct region based on the ventricular wall thicknesses detected for various portions of the RV wall. In another embodiment, use of a plurality of ultrasound transducers such as 132A-B allows for estimation of the size of an infarct region based on the ventricular diameters detected for various planes in the RV. The infraction region is detected as the area associated with minimum ventricular diameter decrease between end diastole and end systole, indicating an akinetic or dyskinetic region. In one embodiment, use of a plurality of ultrasound transducers such as 132A-B allows for estimation of LV diameters and/or volume, in addition to or instead of the RV diameters and/or volume.

Figure 3:
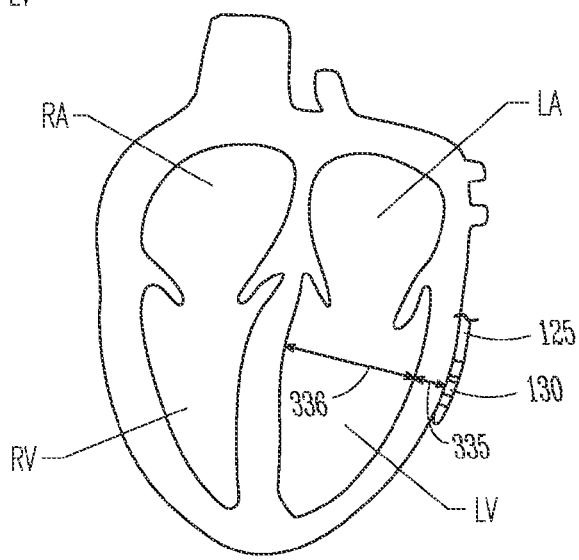
FIG. 3 is an illustration of another embodiment of portions of an implantable lead for detecting cardiac dimensions using ultrasound.

FIG. 3 is an illustration of an embodiment of the distal portion of lead 125. While ultrasound transducer 130 is shown for illustrative purposes, in various embodiments, lead 125 includes any number of ultrasound transducers for placement over the LV. In the illustrated embodiment, ultrasound transducer 130 allows for detection of a ventricular diameter 336 and a ventricular wall thickness 335.

Figure 4:
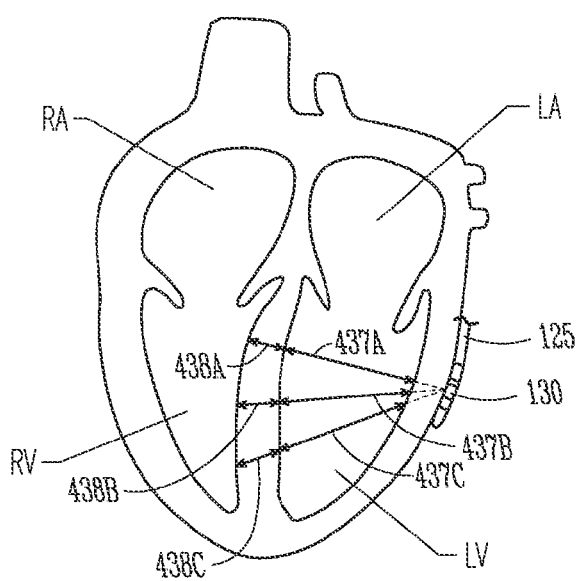
FIG. 4 is an illustration of another embodiment of portions of an implantable lead for detecting cardiac dimensions using ultrasound.

FIG. 4 is an illustration of another embodiment the distal portion of lead 125. In the illustrated embodiment, ultrasound transducer 130 is the phased-array ultrasound transducer with an electronically controlled directionality. The phased-array ultrasound transducer allows for detection of ventricular diameters (e.g., 437A-C) at multiple planes and wall thicknesses (e.g., 438A-C) of the interventricular septum. In one embodiment, the resulting multiple ventricular diameters allow for estimation of the volume of the LV. In another embodiment, the resulting multiple ventricular diameters allow for estimation of the size of an infarct region.

In various embodiments, leads 110, 115, and/or 125 each include one or more ultrasound transducers including, but not limited to, one or more of those illustrated as ultrasound transducers 129, 130, and 132A-B.

Figure 5:
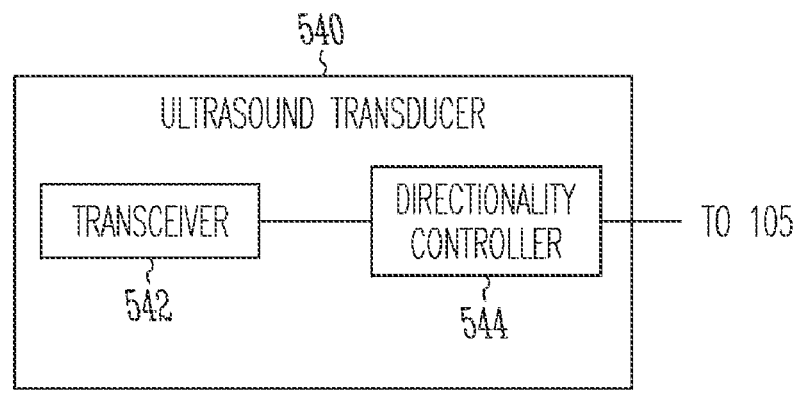
FIG. 5 is a block diagram illustrating an embodiment of an ultrasound transducer with a directionality controller.

FIG. 5 is a block diagram illustrating an embodiment of an ultrasound transducer 540. Ultrasound transducer 540 is to be incorporated into a lead such as lead 110, 115, or 125 and represents an embodiment of ultrasound transducer 129, 130, 132A, or 132B. Ultrasound transducer 540 includes a transceiver 542, and a directionality controller 544. Transceiver 542 transmits an ultrasound signal and receives the reflected ultrasound signal. In one embodiment, transceiver 542 includes at least two ultrasound transducers such as piezoelectric transducers, with one functioning as a transmitter to transmit the ultrasound signal and another functioning as a receiver to receive the reflected ultrasound signal. In another embodiment, transceiver 542 includes at least one ultrasound transducer, such as a piezoelectric transducer, functioning as both the transmitter and the receiver. Directionality controller 544 is electrically coupled to implantable medical device 105 via conductors in lead 110, 115, or 125. In one embodiment, ultrasound transducer 540 is a rotating ultrasound transducer, and directionality controller 544 includes a motor coupled to transceiver 542 to physically steer their directions. In another embodiment, ultrasound transducer 540 is a phased array ultrasound transducer, and directionality controller 544 includes an electronic directionality controller coupled to transceiver 542 to electronically steer its direction.

Figure 6:
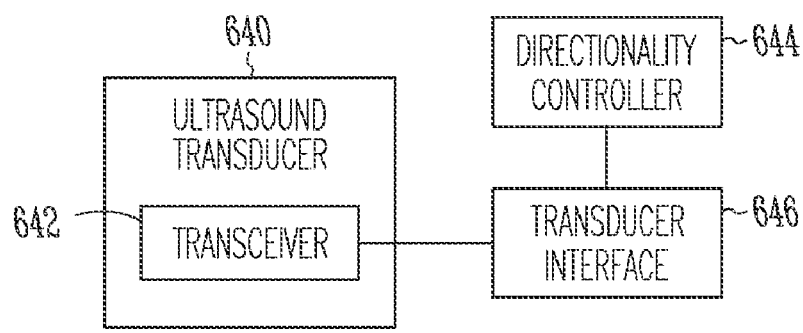
FIG. 6 is a block diagram illustrating another embodiment of an ultrasound transducer with a directionality controller.

FIG. 6 is a block diagram illustrating an embodiment of an ultrasound transducer 640 coupled to a directionality controller 644 through a transducer interface 646. Ultrasound transducer 640 is to be incorporated into a lead such as lead 110, 115, or 125 and represents an embodiment of ultrasound transducer 129, 130, 132A, or 132B. Directionality controller 644 is included in implantable medical device 105. Ultrasound transducer 640 includes a transceiver 642. Transceiver 642 transmits an ultrasound signal and receives the reflected ultrasound signal. In one embodiment, transceiver 642 includes at least two ultrasound transducers such as piezoelectric transducers, with one functioning as a transmitter to transmit the ultrasound signal and another functioning as a receiver to receive the reflected ultrasound signal. In another embodiment, transceiver 642 includes at least one ultrasound transducer, such as a piezoelectric transducer, functioning as both the transmitter and the receiver. In one embodiment, ultrasound transducer 640 is a rotating ultrasound transducer. Directionality controller 644 includes a motor. Transducer interface 646 includes a mechanical linkage in lead 110, 115, or 125 to translate the rotation of the motor to the rotating ultrasound transducer to physically steer the direction of transceiver 642. In another embodiment, ultrasound transducer 640 is a phased array ultrasound transducer. Directionality controller 644 includes an electronic directionality controller. Transducer interface 646 includes conductors in lead 110, 115, or 125 to electrically connect the electronic directionality controller to the phased array ultrasound transducer to electronically steer the direction of transceiver 642.

Figure 7:
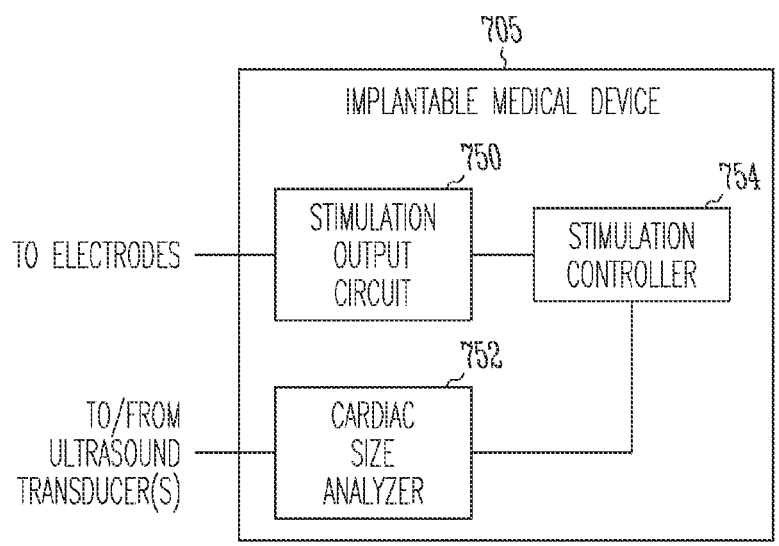
FIG. 7 is a block diagram illustrating an embodiment of portions of a circuit of the implantable medical device.

FIG. 7 is a block diagram illustrating an embodiment of an implantable medical device 705, which represents an embodiment of portions of the circuit of implantable medical device 105. Implantable medical device 705 includes a stimulation output circuit 750, a cardiac size analyzer 752, and a stimulation controller 754. Stimulation output circuit 750 delivers electrical stimulation through electrodes placed in a patient's body. In one embodiment, the electrical stimulation includes cardiac pacing pulses delivered to the heart through pacing electrodes such as those illustrated in FIG. 1. In another embodiment, the electrical stimulation includes neurostimulation delivered to a component of the patient's nervous system through neurostimulation electrodes or transducers. Examples of such component of the nervous system include baroreceptors, aortic nerve, carotid nerve, vagus nerve, the spinal cord dorsal or ventral nerves, the sympathetic ganglia and nerves, and cardiac fat pads. Cardiac size analyzer 752 receives one or more ultrasound signals from one or more ultrasound transducers, such as one or more of ultrasound transducers 129, 130, and 132A-B, and produces one or more cardiac size parameters using the one or more ultrasound signals. In various embodiments, the one or more cardiac size parameters include one or more atrial and/or ventricular size parameters such as cardiac chamber diameter (atrial diameter and ventricular diameter), cardiac chamber volume (atrial volume and ventricular volume), cardiac wall thickness (atrial wall thickness and ventricular wall thickness), infarct size, change in any of these parameters over time or between measurements, and rate of change in any of these parameters. Stimulation controller 754 controls the delivery of the electrical stimulation using the one or more cardiac size parameters.

Figure 8:
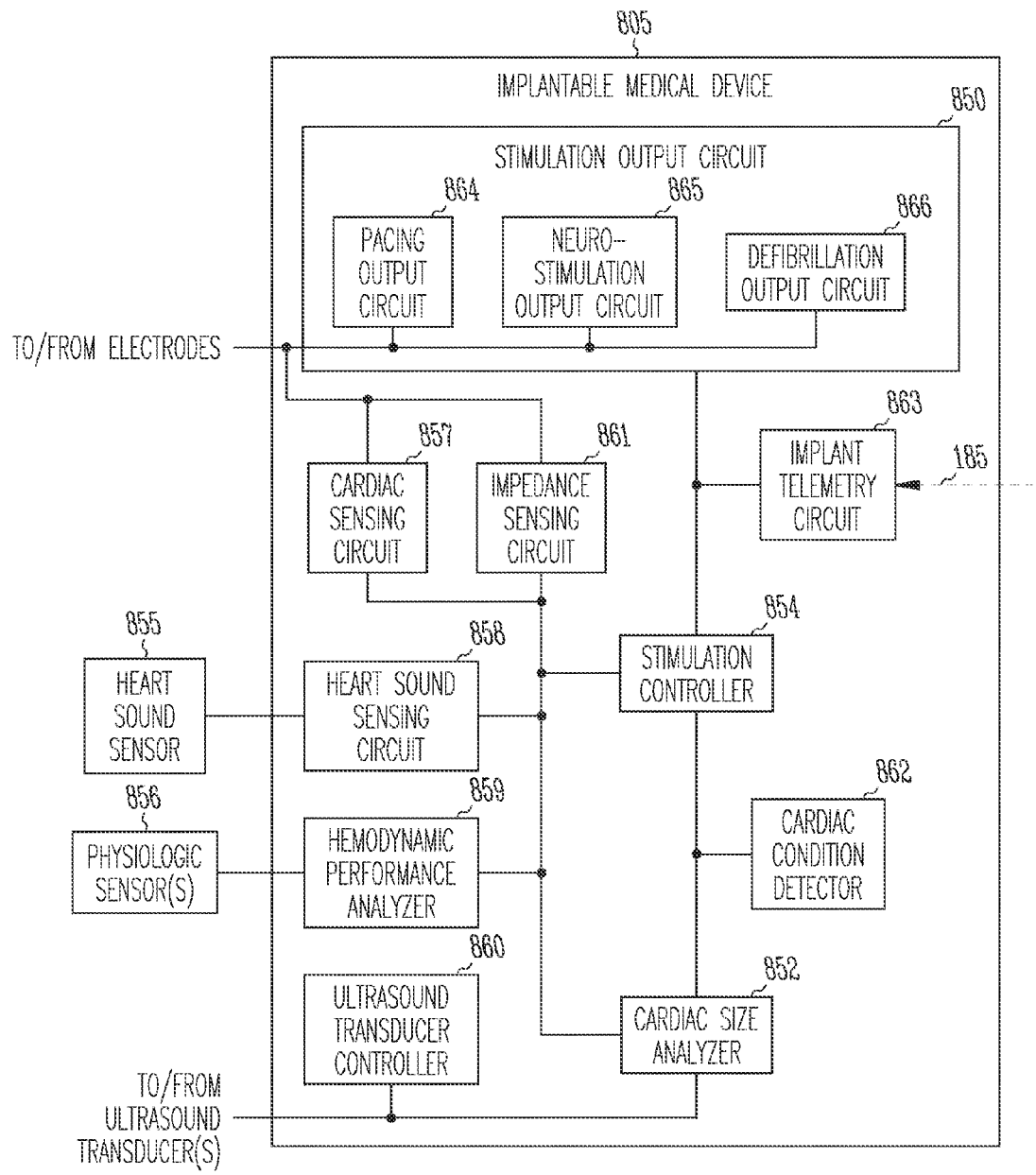
FIG. 8 is a block diagram illustrating another embodiment of portions of the circuit of the implantable medical device.

FIG. 8 is a block diagram illustrating an embodiment of an implantable medical device 805, which represents another embodiment of portions of the circuit of implantable medical device 105 and a specific embodiment of implantable medical device 705. Implantable medical device 805 includes a stimulation output circuit 850, a cardiac sensing circuit 857, a heart sound sensing circuit 858, an impedance sensing circuit 861, a hemodynamic performance analyzer 859, an ultrasound transducer controller 860, a cardiac size analyzer 852, a cardiac condition detector 862, a stimulation controller 854, and an implant telemetry circuit 863. In addition, implantable medical device 805 includes, and/or is connected to, a heart sound sensor 855 and one or more physiologic sensors 856.

Stimulation output circuit 850 is a specific embodiment of stimulation output circuit 750 and delivers electrical stimulation. In the illustrated embodiment, stimulation output circuit 850 includes a pacing output circuit 864 to deliver cardiac pacing pulses, a neurostimulation output circuit 865 to deliver neurostimulation, and a defibrillation output circuit 866 to deliver cardioversion/defibrillation pulses. Cardiac sensing circuit 857 sense one or more cardiac signals. Heart sound sensing circuit 858 receives and processes a signal from heart sound sensor 855 to produce a heart sound signal indicative of heart sounds. Examples of heart sound sensor 855 include an implantable accelerometer and an implantable microphone. Impedance sensing circuit 861 senses an intracardiac impedance signal using electrodes on leads 110, 115, and/or 125. In one embodiment, impedance sensing circuit 861 senses the intracardiac impedance signal by injecting a current through electrodes 120B and 128B and sensing voltage across electrodes 120A and 128A. An example of such impedance sensing is discussed in U.S. Pat. No. 6,728,894, entitled "MULTI-SITE IMPEDANCE SENSOR USING CORONARY SINUS/VEIN ELECTRODES", assigned to Cardiac Pacemakers, Inc., which is incorporated by reference herein in it entirety. The heart sounds and/or the intracardiac impedance are used to time the sampling of the one or more ultrasound signals for producing the one or more cardiac size parameters. Hemodynamic performance analyzer 859 receives one or more physiologic signals indicative of hemodynamic performance from physiologic sensor(s) 856 and produces one or more hemodynamic parameters using the one or more physiologic signals. In one embodiment, physiologic sensor(s) 856 includes one or more pressure sensors to sense blood pressure at one or more vascular locations, and hemodynamic performance analyzer 859 produces hemodynamic parameters indicative of, for example, cardiac output or stroke volume and ventricular synchrony.

Ultrasound transducer controller 860 controls operation of the one or more ultrasound transducers, including the timing and direction of sensing. Cardiac size analyzer 852, which is a specific embodiment of cardiac size analyzer 752, receives one or more ultrasound signals from one or more ultrasound transducers, such as one or more of ultrasound transducers 129, 130, and 132A-B, and produces one or more cardiac size parameters using the one or more ultrasound signals. In one embodiment, cardiac size analyzer 852 also uses the one or more cardiac signals, the heart sound signal, and/or the one or more hemodynamic parameters to gate or time the sampling of the one or more ultrasound signals for producing the one or more cardiac size parameters. Cardiac condition detector 862 detects specified type cardiac conditions using the one or more cardiac size parameters. In one embodiment, the specified type cardiac conditions include adverse conditions resulting from the electrical stimulation. Such adverse conditions indicate a need for stopping or adjusting the electrical stimulation. Stimulation controller 854 is a specific embodiment of stimulation controller 754 and controls delivery of the electrical stimulation using the one or more cardiac size parameters produced by cardiac size analyzer 852 and the specified type cardiac conditions detected by cardiac function detector 862. In the illustrated embodiment, stimulation controller 854 controls the delivery of cardiac pacing, neurostimulation, and/or cardioversion/defibrillation. Implant telemetry 863 receives and transmits data via telemetry link 185. Ultrasound transducer controller 860, cardiac size analyzer 852, cardiac condition detector 862, and a stimulation controller 854 are further discussed below, with reference to FIGS. 9-12.

Figure 9:
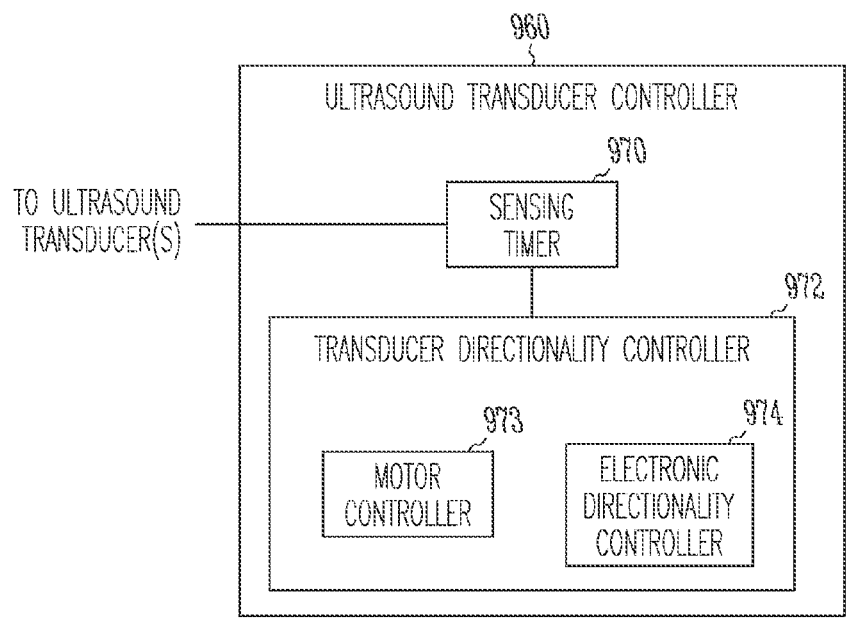
FIG. 9 is a block diagram illustrating an embodiment of an ultrasound transducer controller of the implantable medical device.

FIG. 9 is a block diagram illustrating an embodiment of an ultrasound transducer controller 960, which represents a specific embodiment of ultrasound transducer controller 860. Ultrasound transducer controller 960 includes a sensing timer 970 and a transducer directionality controller 972.

Sensing timer 970 activates the one or more ultrasound transducers for sensing the one or more ultrasound signals. In various embodiments, the one or more ultrasound signals are needed for a certain period of time and/or intermittently, such as according to a specified schedule. In one embodiment, sensing timer 970 activates the one or more ultrasound transducers during an acute therapy parameter evaluation or optimization procedure. In one embodiment, the one or more ultrasound signals are sensed on a periodic basis, such as on a daily or weekly basis, for long-term therapy titration and/or safety check purposes.

Transducer directionality controller 972 controls the directionality of each of the one or more ultrasound transducers when the one or more ultrasound transducers are activated for sensing. Transducer directionality controller 972 produces a direction command specifying a direction for each of the one or more ultrasound transducers and transmits the direction command to directionality controller 544 or 644, which in turn steers the direction of the transducer mechanically or electronically as discussed above. In the illustrated embodiment, transducer directionality controller 972 includes a motor controller 973 and an electronic directionality controller 974. Motor controller 973 produces direction commands each for mechanically controlling the direction of an ultrasound transducer. Electronic directionality controller 974 produces direction commands each for electronically controlling the direction of an ultrasound transducer. In various embodiments, transducer directionality controller 972 includes one or both of motor controller 973 and electronic directionality controller 974, depending on how the directionality of each ultrasound transducer is controlled.

Figure 10:
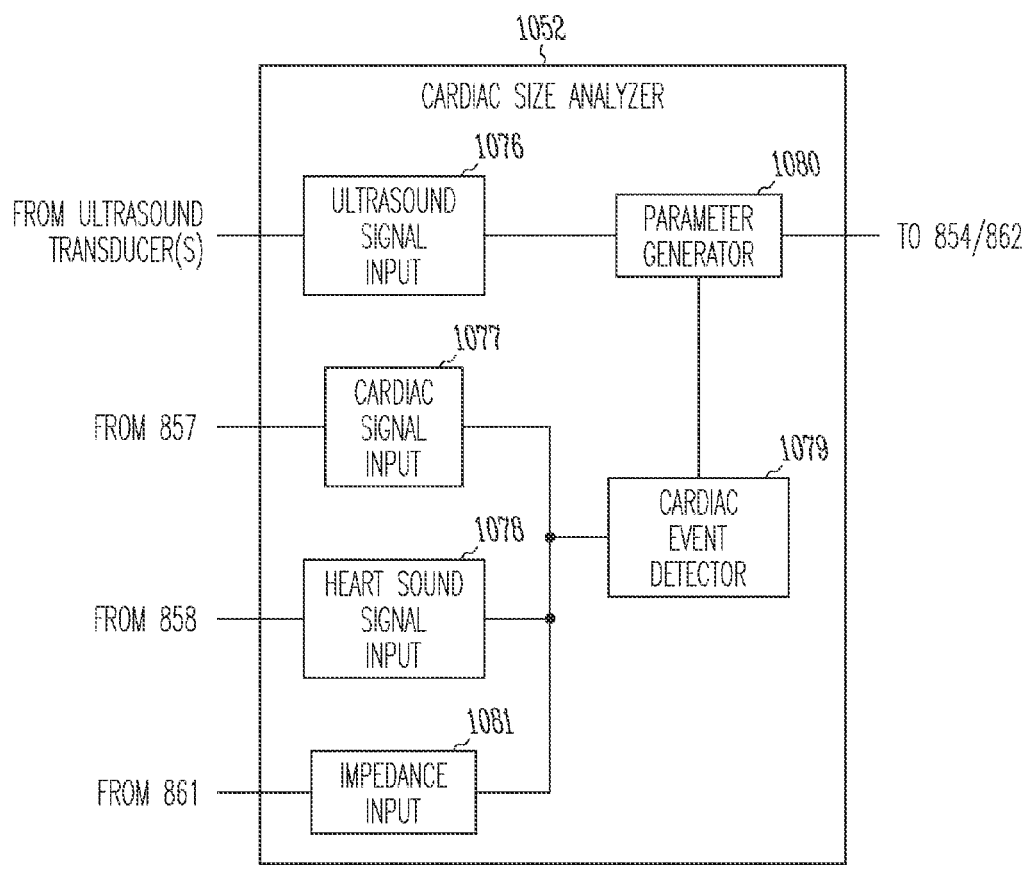
FIG. 10 is a block diagram illustrating an embodiment of a cardiac size analyzer of the implantable medical device.

FIG. 10 is a block diagram illustrating an embodiment of a cardiac size analyzer 1052, which represents a specific embodiment of cardiac size analyzer 852. Cardiac size analyzer 1052 includes an ultrasound signal input 1076, a cardiac signal input 1077, a heart sound signal input 1078, an impedance input 1081, a cardiac event detector 1079, and a parameter generator 1080.

Ultrasound signal input 1076 receives the one or more ultrasound signals from the one or more ultrasound transducers. Cardiac signal input 1077 receives the one or more cardiac signals sensed by cardiac sensing circuit 857. Heart sound input 1078 receives the heart sound signal from heart sound sensing circuit 858. Impedance input 1081 receives the intracardiac impedance signal from impedance sensing circuit 861. Cardiac event detector 1079 detects one or more predetermined type cardiac events from the one or more cardiac signals, the heart sound signal, and/or the intracardiac impedance signal. Examples of such cardiac events include end of systole and end of diastole. Parameter generator 1080 produces the one or more cardiac size parameters by sampling the one or more ultrasound signals in response to the detection of the one or more predetermined type cardiac events. The sampling is so timed because the value of a cardiac size parameter at a particular phase or point of a cardiac cycle may have particular significance. Such timing of sampling also ensures that values for each cardiac size parameter are produced at the same phase/point of cardiac cycles to allow proper comparison indicative of progress of a cardiac condition.

Examples of the cardiac size parameters include: (1) a cardiac chamber diameter parameter representative of a single plane cardiac chamber diameter, (2) a parameter indicative of change in the cardiac chamber diameter parameter; (3) a parameter indicative of rate of change in the cardiac chamber diameter parameter; (4) a cardiac wall thickness parameter representative of a cardiac wall thickness in a cardiac region, (5) a parameter indicative of change in the cardiac wall thickness parameter, (6) a parameter indicative of rate of change in the cardiac wall thickness parameter, (7) a cardiac chamber volume parameter representative of an estimated cardiac chamber volume, (8) a parameter indicative of change in the cardiac chamber volume parameter, (9) a parameter indicative of rate of change in the cardiac chamber volume parameter, (10) an infarct size parameter representative of an estimated infarct size, (11) a parameter indicative of change in the infarct size parameter, and (12) a parameter indicative of rate of change in the infarct size parameter. In one embodiment, the single plane cardiac chamber diameter and the cardiac wall thickness are directly sampled from the one or more ultrasound signals. The cardiac chamber volume is estimated using a plurality of cardiac chamber diameter parameters. The infarct size is estimated using a plurality of the cardiac chamber diameter parameters and/or a plurality of the cardiac wall thickness parameters. The change in each of the one or more cardiac size parameters is the difference in value of a cardiac size parameter between two measurements or over a specified time period. In one embodiment, the specific time period is provided by the specified schedule according to which sensing timer 970 activates the one or more ultrasound transducers. The rate of change in each of the one or more cardiac size parameters is the change in that cardiac size parameter versus time. The rate of change provides trended data of cardiac dimensions. In one embodiment, the rate of change of a cardiac size parameter is the time derivative of that cardiac size parameter.

In one embodiment, parameter generator 1080 also produces one or more parameters indicative of various cardiac conditions and/or hemodynamic performance using the one or more cardiac size parameters. For example, cardiac chamber diameter or volume provides for estimation of ejection fraction. In a specific embodiment, parameter generator 1080 produces a parameter indicative of ejection fraction using the cardiac chamber diameter parameter and/or the cardiac chamber volume parameter. In another specific embodiment, parameter generator 1080 produces a parameter indicative of change in the ejection fraction using the parameter indicative of change in the cardiac chamber diameter parameter and/or the parameter indicative of change in the cardiac chamber volume parameter. In another specific embodiment, parameter generator 1080 produces a parameter indicative rate of change in the ejection fraction using the parameter indicative of rate of change in the cardiac chamber diameter parameter and/or the parameter indicative of rate of change in the cardiac chamber volume parameter.

Figure 11:
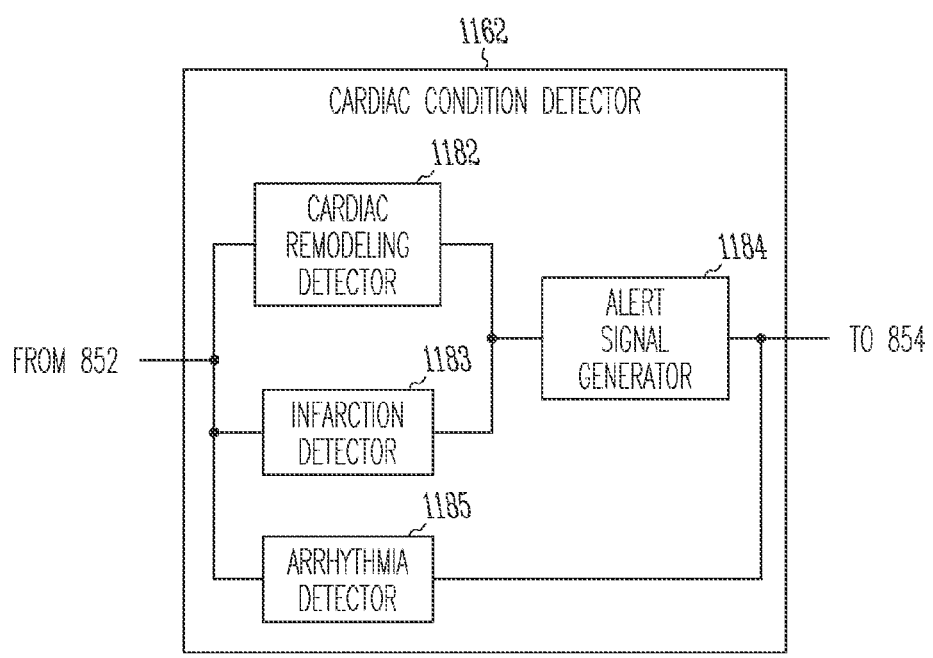
FIG. 11 is a block diagram illustrating an embodiment of a cardiac condition detector of the implantable medical device.

FIG. 11 is a block diagram illustrating an embodiment of a cardiac condition detector 1162, which represents a specific embodiment of cardiac condition detector 862 and detects specified type cardiac conditions. In various embodiments, a specified type cardiac condition is detected when a cardiac size parameter falls out of a predetermined threshold range, such as when a parameter indicative of change in that cardiac size parameter exceeds a predetermined threshold. In the illustrated embodiment, cardiac condition detector 1162 includes a cardiac remodeling detector 1182, an infarction detector 1183, an alert signal generator 1184, and an arrhythmia detector 1185.

Cardiac remodeling detector 1182 detects a degree of cardiac remodeling using the one or more cardiac size parameters and produces a remodeling parameter representative of the detected degree of cardiac remodeling. In various embodiments, cardiac remodeling detector 1182 uses one or more of the cardiac chamber diameter parameters, the parameter indicative of change in the cardiac chamber diameter parameter, the cardiac wall thickness parameter, the parameter indicative of change in the cardiac wall thickness parameter, the cardiac chamber volume parameter, and the parameter indicative of change in the cardiac chamber volume parameter. Infarction detector 1183 detects a degree of infarction using one or more of the infarct size parameter and the parameter indicative of change in the infarct size parameter. Alert signal generator 1184 produces a remodeling alert signal when the remodeling parameter exceeds a predetermined remodeling threshold and an infarction alert signal when the infarction size parameter or the parameter indicative of change in the infarct size parameter exceeds a predetermined infarction threshold. The remodeling alert signal or infarction alert signal is transmitted to stimulation controller 854. In one embodiment, the remodeling alert signal or infarction alert signal are transmitted to implant telemetry circuit 863 for transmission to external system 190 via telemetry link 185 for notifying a physician or caregiver and/or the patient. Arrhythmia detector 1185 detects and classifies tachyarrhythmia episodes using the one or more cardiac size parameters. In one embodiment, arrhythmia detector 1185 detects and classifies tachyarrhythmia episodes by detecting relative changes in one or more cardiac size parameters, such as cardiac chamber diameter and/or volume that are indicative of stroke volume.

Figure 12:
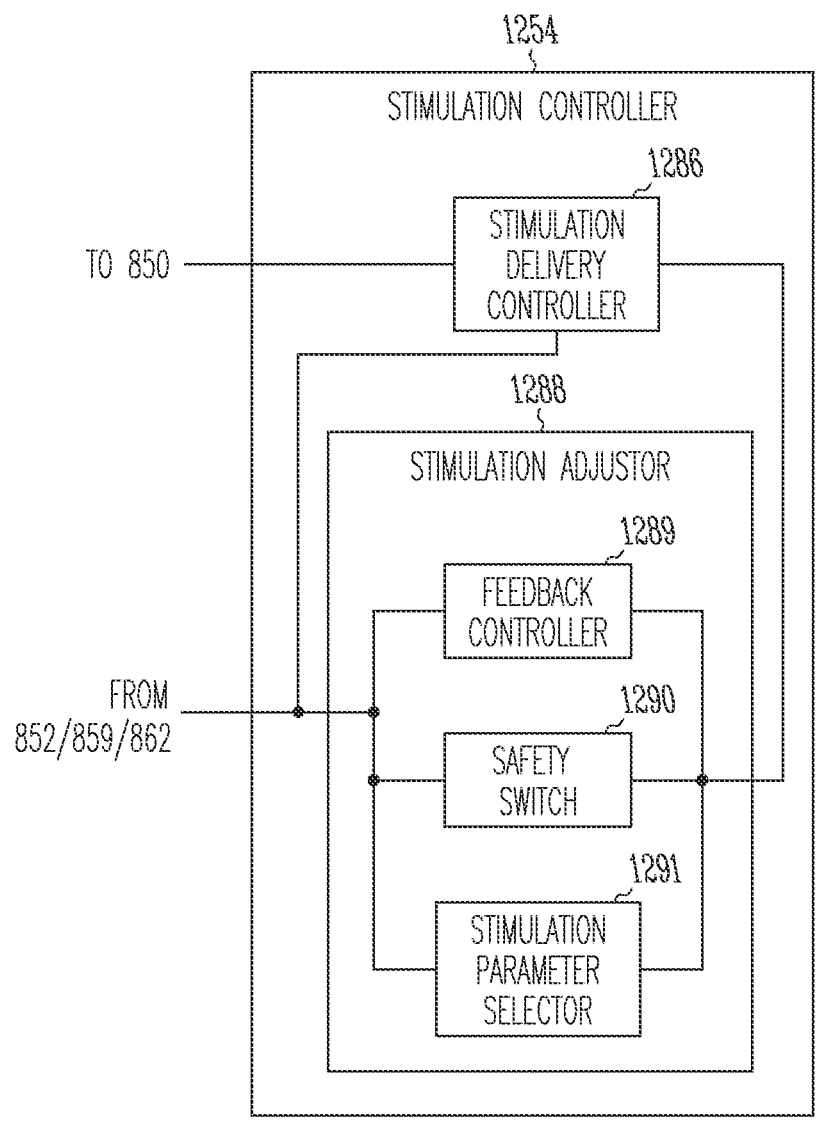
FIG. 12 is a block diagram illustrating an embodiment of a stimulation controller of the implantable medical device.

FIG. 12 is a block diagram illustrating an embodiment of a stimulation controller 1254, which represents a specific embodiment of stimulation controller 854. Stimulation controller 1254 includes a stimulation delivery controller 1286 and a stimulation adjuster 1288.

Stimulation delivery controller 1286 controls the delivery of the electrical stimulation using stimulation parameters. Stimulation adjuster 1288 adjusts the stimulation parameters using at least the one or more cardiac size parameters. In one embodiment, stimulation delivery controller 1286 controls the delivery of the cardiac pacing pulses using pacing parameters. Stimulation adjuster 1288 adjusts the pacing parameters such as pacing on/off, pacing mode, atrioventricular (AV) delay, interventricular delay, intraventricular delay, pacing site, and duty cycle (for intermittent pacing). In one embodiment, stimulation delivery controller 1286 controls the delivery of the neurostimulation pulses using neurostimulation parameters. Stimulation adjuster 1288 adjusts the neurostimulation parameters such as stimulation on/off, pulse amplitude, pulse duration, stimulation frequency (inter-pulse interval), and duty cycle (for intermittent neurostimulation). In one embodiment, stimulation delivery controller 1286 controls the delivery of cardioversion/defibrillation pulses when a tachyarrhythmia episode is detected and classified as a type requiring a cardioversion/defibrillation therapy by arrhythmia detector 1185.

In the illustrated embodiment, stimulation adjuster 1288 includes a feedback controller 1289, a safety switch 1290, and a stimulation parameter selector 1291. In other embodiments, stimulation adjuster 1288 includes any one or more of feedback controller 1289, safety switch 1290, and stimulation parameter selector 1291.

Feedback controller 1289 allows for long-term or short-term titration of the electrical stimulation. In one embodiment, feedback controller 1289 adjusts the stimulation parameters to maintain the effect of the electrical stimulation within a target region defined by one or more values of the one or more cardiac size parameters. In another embodiment, feedback controller 1289 adjusts the stimulation parameters using the one or more cardiac size parameter and the one or more hemodynamic parameters produced by hemodynamic performance analyzer 859. The stimulation parameters are adjusted to maintain the effect of the electrical stimulation within a target region representative of a balance between improving hemodynamic performance and reducing cardiac remodeling. The target region is defined by values of the one or more cardiac size parameter and the one or more hemodynamic parameters.

Safety switch 1290 allows for safety check of the electrical stimulation by initiating, terminating, or adjusting the delivery of the electrical stimulation in response to the detection of a specified type cardiac condition that indicates inefficacy of the electrical stimulation or a condition that is considered intolerably harmful to the patient. In one embodiment, safety switch 1290 stops the delivery of the electrical stimulation in response to the remodeling alert signal or the infarction size alert signal.

Stimulation parameter selector 1291 allows for acute evaluation and selection of stimulation parameters. Stimulation parameter selector 1291 generates multiple sets of stimulation parameters using which stimulation delivery controller 1286 controls the delivery of the electrical stimulation. The one or more ultrasound signals are sensed during the delivery of the electrical stimulation, and sets of the one or more cardiac size parameters are produced, each in association with one of the multiple sets of stimulation parameters. Stimulation parameter selector 1291 selects an optimal set of stimulation parameters from the multiple sets of stimulation parameters based on the sets of the one or more cardiac size parameters each associated with one of the multiple sets of stimulation parameters. For example, the set of stimulation parameters producing the least cardiac wall thickening is selected.

Figure 13:
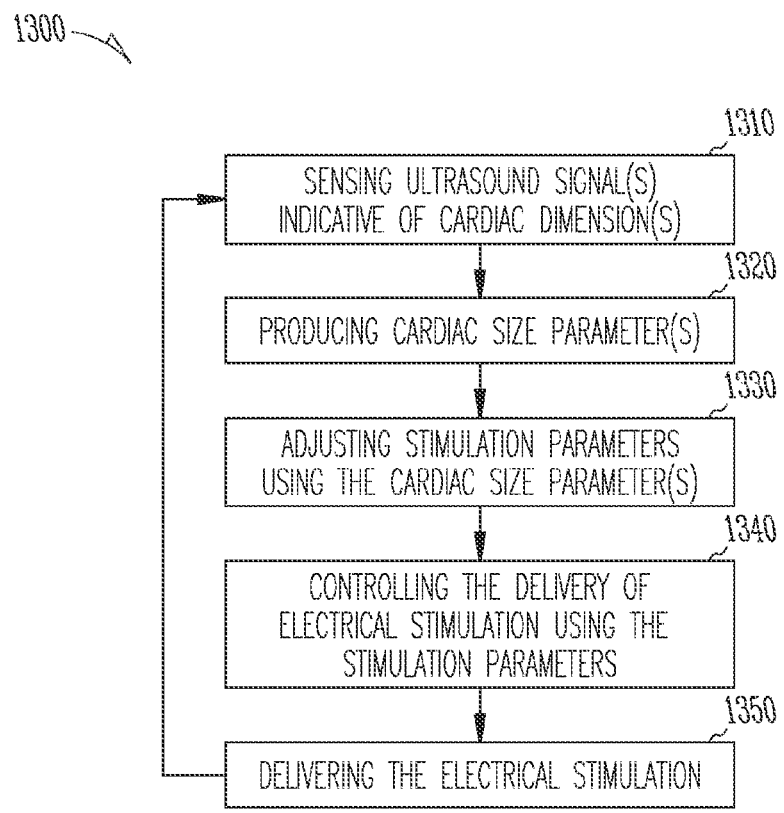
FIG. 13 is a flow chart illustrating an embodiment of a method for controlling electrical stimulation using ultrasonically sensed cardiac dimensions.

FIG. 13 is a flow chart illustrating an embodiment of a method 1300 for controlling electrical stimulation using ultrasonically sensed cardiac dimensions. In one embodiment, the method is performed by system 100.

One or more ultrasound signals indicative of one or more cardiac dimensions are sensed at 1310. The one or more cardiac dimensions are each a distance between two boundary surfaces in the heart. In one embodiment, the one or more ultrasound signals are sensed using one or more implantable ultrasound transducers each incorporated into the distal end of an implantable lead such as a cardiac pacing or defibrillation lead. Each implantable ultrasound transducer includes a transmitter to transmit an ultrasound signal and a receiver to receive the reflected ultrasound signal. In one embodiment, the directionality of each implantable ultrasound transducer is controlled such that multiple cardiac dimensions are detectable using a single ultrasound transducer. In a specific embodiment, the directionality is mechanically controlled by rotating an implantable ultrasound transducer using a motor. In another specific embodiment, a phased array ultrasound transducer is used, and its directionality is electronically controlled. In one embodiment, the one or more ultrasound signals are sensed for a certain period of time and/or according to a specified schedule. In a specific embodiment, the one or more ultrasound signals are sensed on a periodic basis, such as on a daily or weekly basis.

One or more cardiac size parameters are produced using the one or more ultrasound signals at 1320. In one embodiment, the one or more cardiac size parameters are produced by sampling the one or more ultrasound signals during a predetermined type cardiac event such as end of systole or end of diastole. In one embodiment, such a predetermined type cardiac event is detected from one or more cardiac and/or heart sound signals. Examples of the cardiac size parameters include a cardiac chamber diameter parameter representative of a single plane cardiac chamber diameter, a cardiac wall thickness parameter representative of a cardiac wall thickness in a cardiac region, a cardiac chamber volume parameter representative of an estimated cardiac chamber volume, an infarct size parameter representative of an estimated infarct size, parameters each indicative of change in one of the cardiac chamber diameter parameter, cardiac wall thickness parameter, cardiac chamber volume parameter, and infarct size parameter, and parameters each indicative of rate of change in one of the cardiac chamber diameter parameter, cardiac wall thickness parameter, cardiac chamber volume parameter, and infarct size parameter. Such parameters indicate the degree and progress of cardiac remodeling and infarction.

Stimulation parameters for post-MI electrical stimulation are adjusted using the one or more cardiac size parameters at 1330. In one embodiment, the electrical stimulation includes delivery of cardiac pacing pulses using pacing parameters. Examples of pacing parameters adjustable at 1330 include pacing on/off, pacing mode, atrioventricular (AV) delay, interventricular delay, pacing site, and duty cycle (for intermittent pacing). In one embodiment, the electrical stimulation includes delivery of neurostimulation pulses using neurostimulation parameters. Examples of neurostimulation parameters adjustable at 1340 include stimulation on/off, pulse amplitude, pulse duration, stimulation frequency (inter-pulse interval), and duty cycle (for intermittent stimulation). In one embodiment, the stimulation parameters are adjusted in closed-loop control of the electrical stimulation. In a specific embodiment, the stimulation parameters are adjusted as part of a feedback control maintaining the effect of the electrical stimulation within a target region defined by one or more values of the one or more cardiac size parameters.

The delivery of the electrical stimulation is controlled using the stimulation parameters at 1340. The electrical stimulation is delivered at 1350. In one embodiment, the electrical stimulation is delivered on a long-term basis following an acute MI, and 1310-1330 of method 1300 are repeated according to a specified schedule, such as on a periodic basis.

Figure 14:
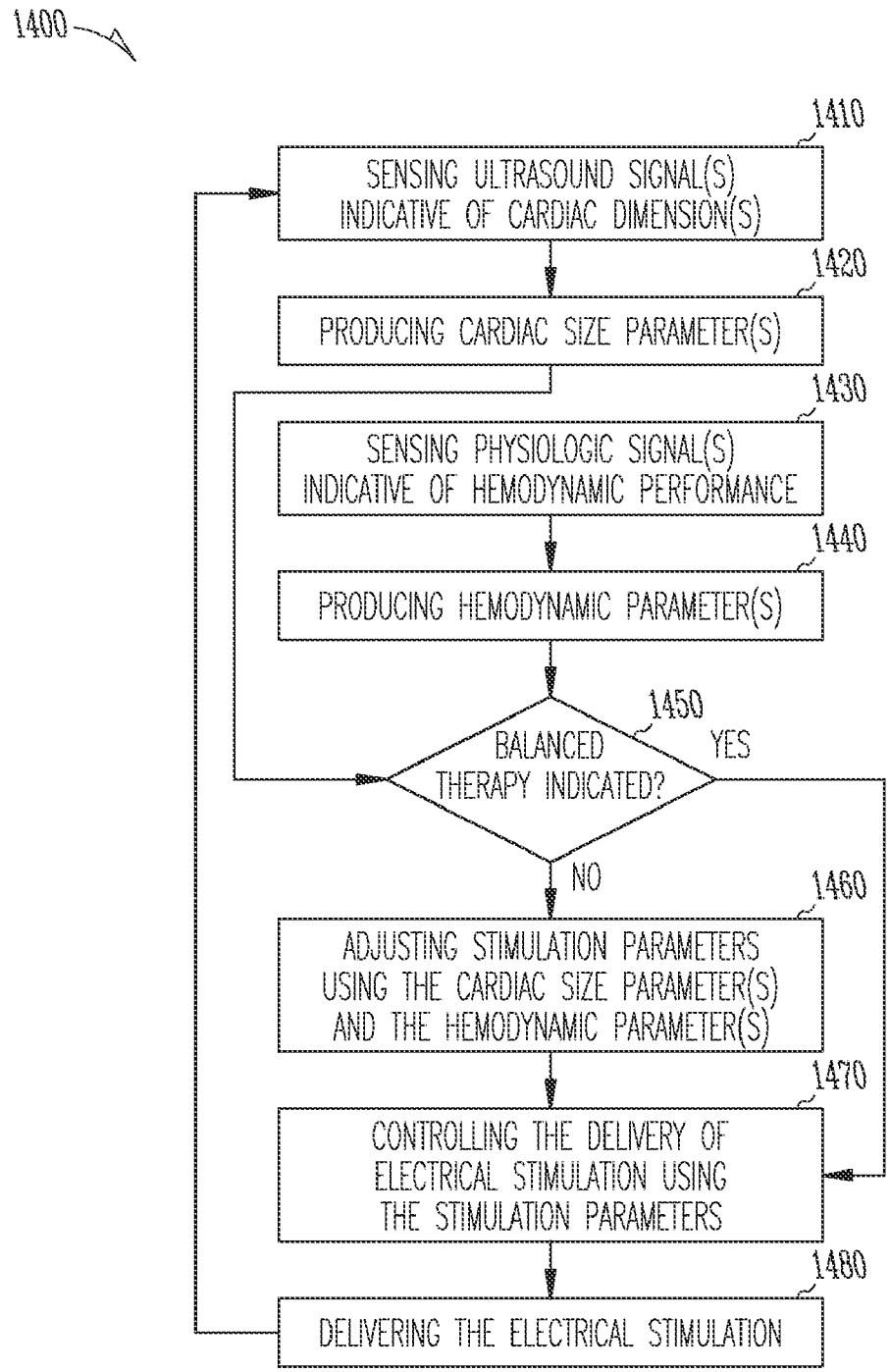
FIG. 14 is a flow chart illustrating an embodiment of a method for feedback control of electrical stimulation using ultrasonically sensed cardiac dimensions and one or more hemodynamic parameters.
Figure 15:
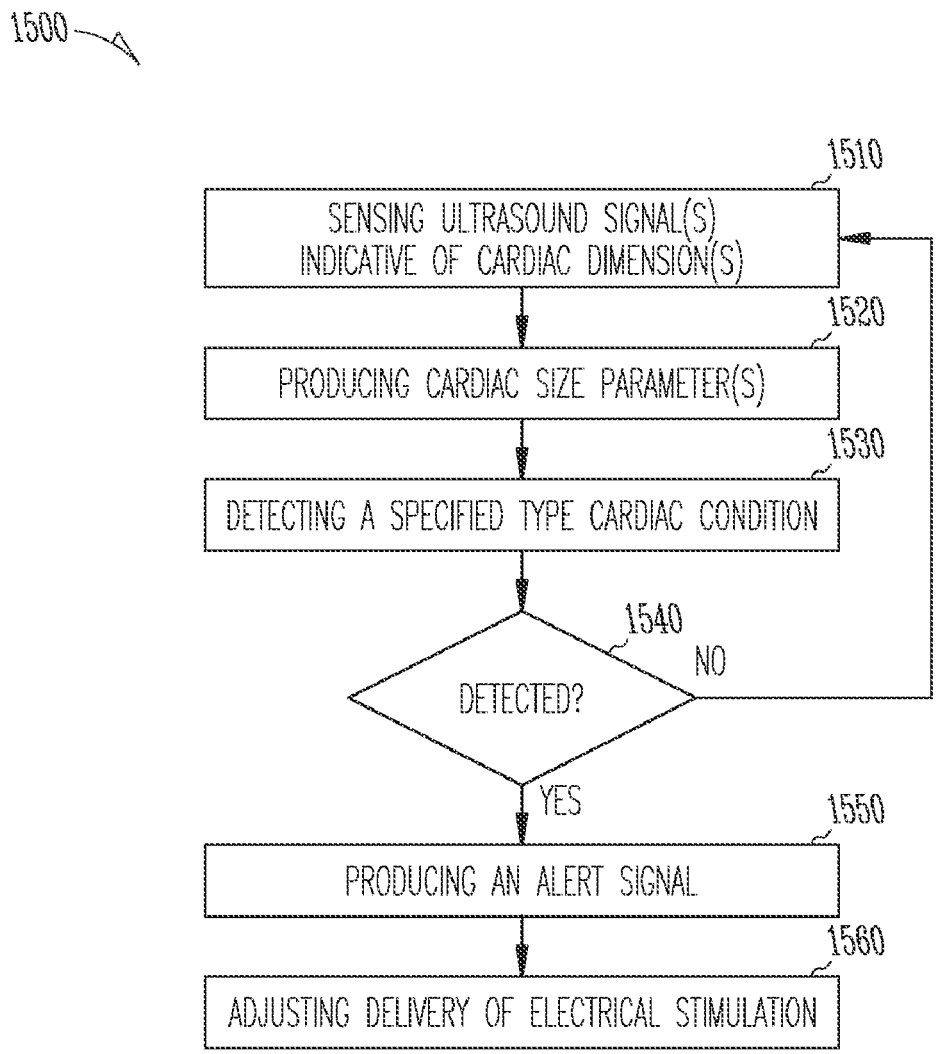
FIG. 15 is a flow chart illustrating an embodiment of a method for controlling delivery of electrical stimulation in response to a cardiac condition detected using ultrasonically sensed cardiac dimensions.
Figure 16:
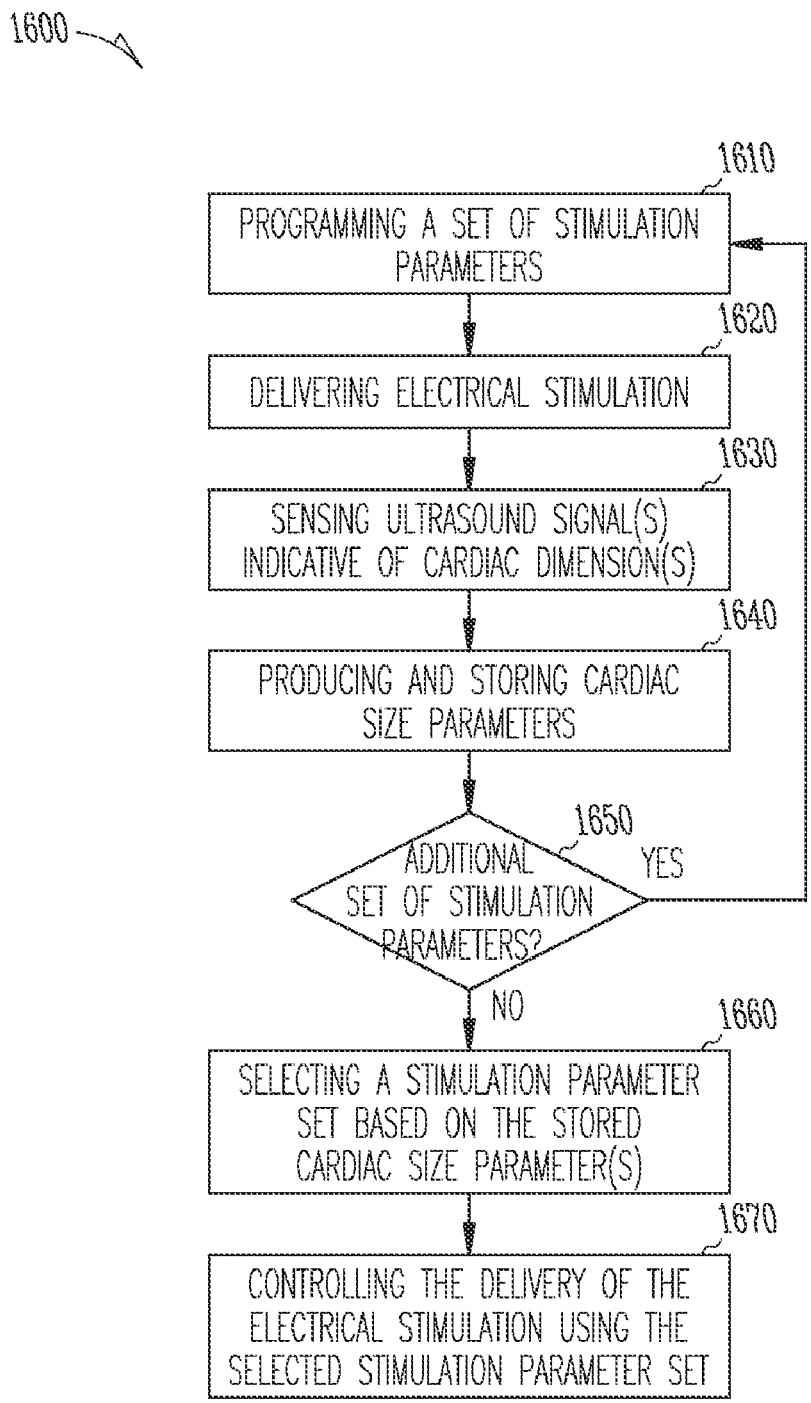
FIG. 16 is a flow chart illustrating an embodiment of a method for optimizing parameters for electrical stimulation using ultrasonically sensed cardiac dimensions.

FIGS. 14-16 illustrate specific examples of adjusting stimulation parameters using at least the one or more cardiac size parameters. Methods 1400, 1500, and 1600, discussed below with reference to FIGS. 14-16, are each a specific embodiment of method 1300. The discussion of the one or more ultrasound signals, the one or more cardiac size parameters, and the electrical stimulation, including the stimulation parameters, for method 1300 generally applies to methods 1400, 1500, and 1600 discussed below.

FIG. 14 is a flow chart illustrating an embodiment of a method 1400 for feedback control of electrical stimulation using hemodynamic performance in addition to the ultrasonically sensed cardiac dimensions. In one embodiment, method 1400 is applied in chronic titration of electrical stimulation for improving hemodynamic performance and controlling ventricular remodeling. When the electrical stimulation is adjusted to improve hemodynamic performance at the risk of comprising remodeling control, or to reduce ventricular remodeling at the risk of compromising hemodynamic performance, method 1400 prevents the electrical stimulation from comprising remodeling control or hemodynamic performance to an unacceptable extent.

The one or more ultrasound signals indicative of one or more cardiac dimensions are sensed at 1410. The one or more cardiac size parameters are produced using the one or more ultrasound signals at 1420. One or more physiologic signals indicative of hemodynamic performance are sensed at 1430. One or more hemodynamic parameters are produced using the one or more physiologic signals at 1440. The one or more hemodynamic parameters indicate a patient's hemodynamic performance, while the one or more cardiac size parameters indicate the degree of the patient's cardiac remodeling.

If a balanced post-MI therapy is indicated at 1450, the delivery of the electrical stimulation is controlled using the current (unchanged) stimulation parameters at 1470, and the electrical stimulation is continued to be delivered at 1480. The balanced post-MI therapy means that the effect of the electrical stimulation is within a target region defined by predetermined values of the one or more cardiac size parameters and the one or more hemodynamic parameters. The target region indicates that the electrical stimulation has balanced effects in hemodynamic performance improvement and cardiac remodeling control.

If the balanced post-MI therapy is not indicated at 1450, the stimulation parameters are adjusted using the one or more cardiac size parameters and the one or more hemodynamic parameters at 1460. The delivery of the electrical stimulation is controlled using the adjusted stimulation parameters at 1470, and the electrical stimulation is continued to be delivered at 1480. The stimulation parameters are adjusted at 1470 until the balanced post-MI therapy is indicated at 1450.

FIG. 15 is a flow chart illustrating an embodiment of a method 1500 for controlling delivery of electrical stimulation in response to cardiac conditions detected using ultrasonically sensed cardiac dimensions. In one embodiment, method 1500 is applied as a safety check during the delivery of post-MI electrical stimulation. For example, when the one or more cardiac size parameters indicate that a current therapy is ineffective or produces potentially harmful effects, electrical stimulation is initiated, terminated, or adjusted.

The one or more ultrasound signals indicative of one or more cardiac dimensions are sensed at 1510. The one or more cardiac size parameters are produced using the one or more ultrasound signals at 1520. A specified type cardiac condition is detected using the one or more cardiac size parameters at 1530. The specified type cardiac condition is detected when at least one of the one or more cardiac size parameters falls out of a threshold range. In one embodiment, the specified type cardiac condition is detected when the parameter indicative of change in at least one of the one or more cardiac size parameters exceeds a threshold. If the specified type cardiac condition is detected at 1540, an alert signal is produced at 1550. The delivery of the electrical stimulation is adjusted in response to the alert signal at 1560. In various embodiments, the adjustment includes initiation or termination of the electrical stimulation or adjustment of the stimulation parameters, depending on the nature and purpose of the electrical stimulation. In one embodiment, the alert signal is also used to notify a physician or other caregiver of the detection of the specified type cardiac condition.

In a specific embodiment, a degree of cardiac remodeling is detected using the one or more cardiac size parameters, and a remodeling parameter representative of the detected degree of cardiac remodeling is produced. The one or more cardiac size parameters used to detect the degree of cardiac remodeling include one or more of the cardiac chamber diameter parameter, the parameter indicative of change in the cardiac chamber diameter parameter, the cardiac wall thickness parameter, the parameter indicative of change in the cardiac wall thickness parameter, the cardiac chamber volume parameter, and the parameter indicative of change in the cardiac chamber volume parameter. The specified type cardiac condition is detected at 1540 when the remodeling parameter exceeds a predetermined threshold. In another specific embodiment, the specified type cardiac condition is detected at 1540 when the infarct size parameter or the parameter indicative of change in the infarct size parameter exceeds a predetermined threshold.

FIG. 16 is a flow chart illustrating an embodiment of a method 1600 for optimizing parameters for electrical stimulation using ultrasonically sensed cardiac dimensions. In one embodiment, method 1600 allows for acute evaluation or optimization of the stimulation parameters for a post-MI therapy. For example, electrical stimulation is delivered using a sequence of different stimulation parameter sets while the one or more ultrasound signals are sensed. One of the stimulation parameter sets is selected for producing the most desirable therapeutic effects.

A set of stimulation parameters is programmed at 1610. The set of stimulation parameters is one of multiple predetermined stimulation parameter sets. The electrical stimulation is delivered using the programmed stimulation parameters at 1620. The one or more ultrasound signals indicative of one or more cardiac dimensions are sensed at 1630. The one or more cardiac size parameters are produced using the one or more ultrasound signals and stored at 1640.

If at least one additional set of stimulation parameters has not been tested at 1650, method 1600 continues from 1610. This allows all of the multiple predetermined stimulation parameter sets to be tested, and all the values of the one or more cardiac size parameters associated with the multiple predetermined stimulation parameter sets are stored. A stimulation parameter set is selected from the multiple predetermined stimulation parameter sets based on the stored values of the one or more cardiac size parameters at 1660. In one embodiment, the stimulation parameter set associated with the smallest degree of change in the cardiac wall thickness parameter is selected from the stimulation parameter sets at 1660. The delivery of the electrical stimulation is controlled using the selected stimulation parameter set at 1670.

It is to be understood that the above detailed description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A system for applying electrical stimulation to a living body having a heart having boundary surfaces and a right atrium (RA), a left atrium (LA), a right ventricle (RV), a left ventricle (LV), and a coronary vein, the system comprising:
   one or more implantable ultrasound transducers adapted to sense one or more ultrasound signals indicative of one or more cardiac dimensions, the one or more implantable ultrasound transducers each including a transceiver adapted to transmit a signal and receive a reflected signal being the signal transmitted by the transceiver and reflected from one of the boundary surfaces; and
   an implantable medical device comprising:
      a stimulation output circuit to deliver the electrical stimulation;
      a cardiac size analyzer adapted to receive the one or more ultrasound signals and produce one or more cardiac size parameters using the one or more ultrasound signals, the one or more cardiac size parameters including one or more of:
         an infarct size parameter representative of an estimated size of an infarct region;
         a parameter indicative of change in the infarct size parameter; and
         a parameter indicative of rate of change in the infarct size parameter; and
      a stimulation controller coupled to the stimulation output circuit, the stimulation controller including:
         a stimulation delivery controller adapted to control the delivery of the electrical stimulation using stimulation parameters; and a stimulation adjustor adapted to adjust the stimulation parameters using the one or more cardiac size parameters.

2. The system of claim 1, wherein the stimulation output circuit comprises a pacing output circuit to deliver cardiac pacing pulses, and the stimulation controller is adapted to control the delivery of the cardiac pacing pulses.

3. The system of claim 1, wherein the stimulation output circuit comprises a neurostimulation output circuit to deliver neurostimulation, and the stimulation controller is adapted to control the delivery of the neurostimulation.

4. The system of claim 1, wherein the stimulation output circuit comprises a defibrillation output circuit to deliver cardioversion/defibrillation pulses, and the stimulation controller is adapted to control the delivery of the cardioversion/defibrillation pulses.

5. The system of claim 1, wherein the implantable medical device comprises one or more of a cardiac sensing circuit to sense a cardiac signal, a heart sound sensing circuit to sense a heart sound signal, and an impedance sensing circuit to sense an intracardiac impedance signal; the cardiac size analyzer comprises an event detector adapted to detect one or more predetermined type cardiac events from one or more of the cardiac signal, the heart sound signal, and the intracardiac impedance signal; and the cardiac size analyzer is adapted to produce the one or more cardiac size parameters by sampling the one or more ultrasound signals in response to the detection of the one or more predetermined type cardiac events.

6. The system of claim 5, wherein the cardiac size analyzer is adapted to produce a cardiac wall thickness parameter representative of a cardiac wall thickness in a cardiac region.

7. The system of claim 6, wherein the cardiac size analyzer is adapted to produce a parameter indicative of change in the cardiac wall thickness parameter.

8. The system of claim 6, wherein the cardiac size analyzer is adapted to produce a parameter indicative of rate of change in the cardiac wall thickness parameter.

9. The system of claim 1, wherein the stimulation adjuster comprises a feedback controller adapted to adjust the stimulation parameters to maintain an effect of the electrical stimulation within a target region defined by at least one or more values of the one or more cardiac size parameters.

10. The system of claim 9, wherein the feedback controller is adapted to adjust the stimulation parameters to maintain the effect of the electrical stimulation within a target region defined by one or more values of the one or more cardiac size parameters and one or more values of one or more hemodynamic parameters, wherein the implantable medical device comprises a hemodynamic performance analyzer adapted to produce the one or more hemodynamic parameters using one or more physiologic signals, and further comprising one or more implantable physiologic sensors coupled to the hemodynamic performance analyzer and adapted to sense the one or more physiologic signals.

11. The system of claim 1, wherein the stimulation adjustor comprises a safety switch adapted to initiate, terminate, or adjust the delivery of the electrical stimulation in response to an alert signal indicative of a detection of a specified type cardiac condition.

12. The system of claim 11, wherein the cardiac size analyzer comprises:
a cardiac remodeling detector adapted to detect a degree of cardiac remodeling using the one or more cardiac size parameters and produce a remodeling parameter representative of the detected degree of cardiac remodeling; and an alert signal generator adapted to generate a remodeling alert signal when the remodeling parameter exceeds a predetermined threshold,
and wherein the safety switch is adapted to initiate, terminate, or adjust the delivery of the electrical stimulation in response to the remodeling alert signal.

13. The system of claim 11, wherein the cardiac size analyzer comprises
an alert signal generator adapted to generate an infarction alert signal when the one or more cardiac size parameters exceeds a predetermined threshold,
and wherein the safety switch is adapted to initiate, terminate, or adjust the delivery of the electrical stimulation in response to the infarction alert signal.

14. The system of claim 1, wherein the stimulation adjustor comprises a stimulation parameter selector adapted to receive values of the one or more cardiac size parameters associated with multiple sets of stimulation parameters and select an optimal set of stimulation parameters from the multiple sets of stimulation parameters based on the values of the one or more cardiac size parameters.

15. The system of claim 1, wherein the cardiac size analyzer is adapted to produce one or more of:
a cardiac chamber diameter parameter representative of a single plane cardiac chamber diameter;
a parameter indicative of change in the cardiac chamber diameter parameter;
a parameter indicative of rate of change in the cardiac chamber diameter parameter;
a cardiac chamber volume parameter representative of an estimated cardiac chamber volume;
a parameter indicative of change in the cardiac chamber volume parameter; and
a parameter indicative of rate of change in the cardiac chamber volume parameter.

16. The system of claim 15, wherein the cardiac size analyzer is adapted to produce one or more of:
a parameter indicative of ejection fraction, using at least one of the cardiac chamber diameter parameter and the cardiac chamber volume parameter;
a parameter indicative of change in the ejection fraction, using at least one of the parameter indicative of change in the cardiac chamber diameter parameter and the parameter indicative of change in the cardiac chamber volume parameter; and
a parameter indicative of rate of change in the ejection fraction, using at least one of the parameter indicative of rate of change in the cardiac chamber diameter parameter and the parameter indicative of rate of change in the cardiac chamber volume parameter.

17. The system of claim 1, further comprising an implantable lead including:
a proximal end configured to be coupled to the implantable medical device;
a distal portion configured to be placed in or about the heart, the distal portion including the one or more implantable ultrasound transducers; and
an elongate body coupled between the proximal end and the distal portion.

18. The lead of claim 17, wherein the one or more implantable ultrasound transducers comprise at least one rotating ultrasound transducer configured to sense a plurality of distances in a plane and having a mechanically controlled directionality.

19. The lead of claim 18, wherein the distal portion comprises a motor coupled to the at least one rotating ultrasound transducer.

20. The lead of claim 19, wherein the distal portion comprises a plurality of rotating ultrasound transducers.

21. The lead of claim 17, wherein the one or more implantable ultrasound transducers comprise one or more phased array ultrasound transducers each including a plurality of transducer elements and having an electronically controlled directionality.

22. The lead of claim 17, wherein the distal portion is configured to be placed in the RA, and the one or more ultrasound transducers are adapted to sense one or more ultrasound signals indicative of one or more atrial dimensions.

23. The lead of claim 17, wherein the distal portion is configured to be placed in the RV, and the one or more ultrasound transducers are adapted to sense one or more ultrasound signals indicative of one or more ventricular dimensions.

24. The lead of claim 17, wherein the distal portion is configured to be placed in the coronary vein over the LV, and the one or more ultrasound transducers are adapted to sense one or more ultrasound signals indicative of one or more ventricular dimensions.

25. The system of claim 1, wherein the cardiac size analyzer is adapted to produce one or more of:
 a cardiac wall thickness parameter representative of a cardiac wall thickness in a cardiac region;
 a parameter indicative of change in the cardiac wall thickness parameter; and
 a parameter indicative of rate of change in the cardiac wall thickness parameter.

26. A system for applying electrical stimulation to a living body having a heart having boundary surfaces and an infarct region, the system comprising:
 one or more implantable ultrasound transducers adapted to sense one or more ultrasound signals indicative of one or more cardiac dimensions, the one or more implantable ultrasound transducers each including a transceiver adapted to transmit a signal and receive a reflected signal being the signal transmitted by the transceiver and reflected from one of the boundary surfaces; and
 an implantable medical device comprising:
  a stimulation output circuit to deliver the electrical stimulation;
  one or more of a cardiac sensing circuit to sense a cardiac signal, a heart sound sensing circuit to sense a heart sound signal, and an impedance sensing circuit to sense an intracardiac impedance signal;
  a cardiac size analyzer including an event detector adapted to detect one or more predetermined type cardiac events from one or more of the cardiac signal, the heart sound signal, and the intracardiac impedance signal, the cardiac size analyzer adapted to receive the one or more ultrasound signals and produce one or more cardiac size parameters including an infarct size parameter representative of an estimated size of the infarct region by sampling the one or more ultrasound signals in response to the detection of the one or more predetermined type cardiac events; and
  a stimulation controller coupled to the stimulation output circuit, the stimulation controller including:
   a stimulation delivery controller adapted to control the delivery of the electrical stimulation using stimulation parameters; and
   a stimulation adjustor adapted to adjust the stimulation parameters using the one or more cardiac size parameters.

27. The system of claim 26, wherein the cardiac size analyzer is adapted to produce a parameter indicative of change in the infarct size parameter.

28. The system of claim 26, wherein the cardiac size analyzer is adapted to produce a parameter indicative of rate of change in the infarct size parameter.

29. The system of claim 26, wherein the stimulation adjuster comprises a feedback controller adapted to adjust the stimulation parameters to maintain an effect of the electrical stimulation within a target region defined by at least one or more values of the one or more cardiac size parameters.

30. The system of claim 29, wherein the feedback controller is adapted to adjust the stimulation parameters to maintain the effect of the electrical stimulation within a target region defined by one or more values of the one or more cardiac size parameters and one or more values of one or more hemodynamic parameters, wherein the implantable medical device comprises a hemodynamic performance analyzer adapted to produce the one or more hemodynamic parameters using one or more physiologic signals, and further comprising one or more implantable physiologic sensors coupled to the hemodynamic performance analyzer and adapted to sense the one or more physiologic signals.

31. The system of claim 29, wherein the stimulation output circuit comprises a pacing output circuit to deliver cardiac pacing pulses, and the stimulation controller is adapted to control the delivery of the cardiac pacing pulses.

32. The system of claim 29, wherein the stimulation output circuit comprises a neurostimulation output circuit to deliver neurostimulation, and the stimulation controller is adapted to control the delivery of the neurostimulation.

* * * * *